US012797221B2

(12) United States Patent
Ruetenik

(10) Patent No.: US 12,797,221 B2

(45) **Date of Patent: *Nov. 17, 2026**

(54) DISTRACTOR APPARATUS AND METHOD

(71) Applicant: Monty L. Ruetenik, Clear Lake Shores, TX (US)

(72) Inventor: Monty L. Ruetenik, Clear Lake Shores, TX (US)

(73) Assignee: Monty L. Ruetenik, Clear Lake Shores, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/388,782

(22) Filed: Nov. 13, 2025

(65) Prior Publication Data

US 2026/0069444 A1 Mar. 12, 2026

Related U.S. Application Data

(63) Continuation-in-part of application No. 18/091,593, filed on Dec. 30, 2022, now Pat. No. 12,491,101, which is a continuation-in-part of application No. 16/919,810, filed on Jul. 2, 2020, now abandoned, which is a continuation-in-part of application No. 15/727,738, filed on Oct. 9, 2017, now abandoned.

(60) Provisional application No. 62/407,783, filed on Oct. 13, 2016.

(51) Int. Cl.

*A61F 5/01* (2006.01)

*A61F 5/048* (2006.01)

(52) U.S. Cl.

CPC .......... *A61F 5/0125* (2013.01); *A61F 5/0127* (2013.01)

(58) Field of Classification Search

CPC .................... A61F 5/0123; A61F 5/048; A61F 2005/0158; A61F 2005/0165; A61F 5/0111; A61F 5/012; A61F 5/042; A61F 5/05816; A61F 5/0106; A61H 2201/1246; A61H 2201/1642; A61H 2201/1238; A61H 2201/1409; A61H 2201/165; A61H 2201/1664; A61H 2201/1676; A61H 2201/5071; A61H 1/024

See application file for complete search history.

(56) References Cited

U.S. PATENT DOCUMENTS

| | | | | |
|---|---|---|---|---|
| 5,337,737 A * | 8/1994 | Rubin | A63B 23/1281 | |
| | | | 482/111 | |
| 5,547,464 A * | 8/1996 | Luttrell | A61H 1/024 | |
| | | | 482/111 | |
| 5,672,152 A | 9/1997 | Mason et al. | | |
| 5,827,208 A | 10/1998 | Mason et al. | | |
| 7,235,059 B2 | 6/2007 | Mason et al. | | |
| 9,474,675 B2 | 10/2016 | Hansen | | |
| 12,491,101 B2 * | 12/2025 | Ruetenik | A61F 5/0106 | |

(Continued)

FOREIGN PATENT DOCUMENTS

WO WO-2021149908 A1 * 7/2021 ............... A61F 5/32

*Primary Examiner* — Tarla R Patel

(74) *Attorney, Agent, or Firm* — Boulware & Valoir PLLC

(57) ABSTRACT

Apparatus and method for distraction (stretching and/or straightening) of injured joints wherein an upper brace is affixed above the joint, and a lower brace is affixed below the joint. The two braces are connected by cylinders comprising pistons on either side of the joint. A pump then applies cyclical pressures extend and retract the pistons, thereby extending and retracting the joint.

19 Claims, 6 Drawing Sheets

(56) References Cited

U.S. PATENT DOCUMENTS

| | | | | |
|---|---|---|---|---|
| 2015/0051527 | A1* | 2/2015 | Potter | A61F 5/0125 602/16 |
| 2015/0209214 | A1* | 7/2015 | Herr | A61H 1/0266 623/27 |
| 2017/0239119 | A1* | 8/2017 | Stewart | A61G 13/1245 |

* cited by examiner

DISTRACTOR APPARATUS AND METHOD

CROSS-REFERENCE TO RELATED APPLICATIONS

This application is a continuation-in-part of U.S. Ser. No. 18/091,593 filed Dec. 30, 2022, which is a is a continuation-in-part of U.S. patent application Ser. No. 16/919,810, filed Jul. 2, 2020, which is in turn a continuation-in-part of U.S. patent application Ser. No. 15/727,738 filed Oct. 9, 2017 and claims the benefit and priority from U.S. Provisional Patent Application 62/407,783, filed Oct. 13, 2016, the contents and disclosure of each are incorporated herein by reference for all purposes.

FIELD OF THE DISCLOSURE

This disclosure relates to apparatus and methods for distraction (the stretching and/or straightening, usually repeated cyclically) of injured joints, such as knee, ankle, elbow and the like.

BACKGROUND

In the medical context, "distraction" of joints refers to the separation of joint surfaces without rupture of their binding ligaments and without displacement. Distraction is used in a physical therapy context to rehabilitate a joint injured by breakage, osteoarthritis, torn ligaments, reduce pain, and the like, stretching the joint to gradually improve motor function, reduce pain and induce healing. The stretching may be static (stretch and hold or a period of time) or may be cyclically, including repeat stretch/retraction cycles. Combinations are also possible.

After knee surgery and/or in rehabilitation of sore and injured knees, for example, it is important to distract (stretch or uncouple) the knee joint to prevent stiffness from becoming permanent. In athletes, distraction is frequently accomplished by having a trainer or physical therapist pull on the leg to distract the knee joint for a predetermined time period—10 to 20 minutes is customary. In some rehabilitation and physical therapy situations, bungee cords are attached to the ankle or a leg that has an injured knee, while the patient lies down with the cord under tension—stretching or uncoupling the knee joint. Bungee cords of varying elasticities allow customization of the tension applied.

These methods, however, either require manual assistance or a controlled environment (therapy session) to be satisfactorily applied. A detailed description of the problems in knee rehabilitation and the need for stretching is described in published application US20140088466, together with a complicated apparatus for use in therapy, the disclosure of which is incorporated herein by reference.

Prior art distraction methods are somewhat difficult to apply with precision—the tension and speed being somewhat variable—and thus it is not uncommon to further irritate or re-injure the joint with manual distraction. In addition, the need for competent technicians raises costs and in many instances the needed personnel are not available.

Thus, what is needed in the art are better methods of distracting injured joints. The ideal method would be very repeatable, with precise application of tension, speed, degree of stretch, and the like, would be capable of setting a desired tension, speed, degree of stretch, and the like, and would not require dedicated technicians throughout the rehabilitation. Ideally, the rehabilitation could even be performed at home.

This invention addresses one or more of these needs.

SUMMARY OF INVENTION

Generally speaking the invention is a device that braces to the patient above and below the injured joint, and the upper and lower braces are connected via fluid (liquid or gas) driven pistons that are connected to a pump and gauges or sensors to allow consisted repeated application of fluid to extend the pistons, removal of that fluid and e.g., springs allow the pistons to reset. Flexion set means to control the degree of movement are also included and may be mechanical or processor based.

A mechanical flexion set means is simple, reliable and can control the degree of extension and be set by the user, gradually increasing the extent of the distraction. If the pump is controlled by a processor, then speed and pressure and the like can easily be controlled by the programming. In such application, differing pressures can control the degree of extension, increasing pressuring increasing extension.

DETAILED DESCRIPTION

As applied to the knee joint, the invention is an apparatus and method for distraction (stretching and/or straightening) of injured or repaired knee joints. The apparatus comprises pneumatic or hydraulic cylinders that are designed to be disposed on either side of a leg with a knee to be treated. It is important that a cylinder be placed on each side of the leg to prevent twisting and equalize the pull on the knee joint. If only on one side it is likely that the knee would be pulled sidewise as well as downward.

Cylinders are attached to a knee brace or other leg-holding device, secured above the knee joint, and attached to another device secured around the ankle of the leg. The leg-holding device and ankle device are not connected nor hinged together, except via the cylinders. When the cylinder is activated, (piston extended) the knee brace and ankle device are separated (moved apart) thus causing the knee joint to be straightened or slightly separated. The cylinders may be hydraulic (liquid driven) or pneumatic (gas driven) and for simplicity and cost, air pumps are preferred for driving the cylinders.

Figure 1A:
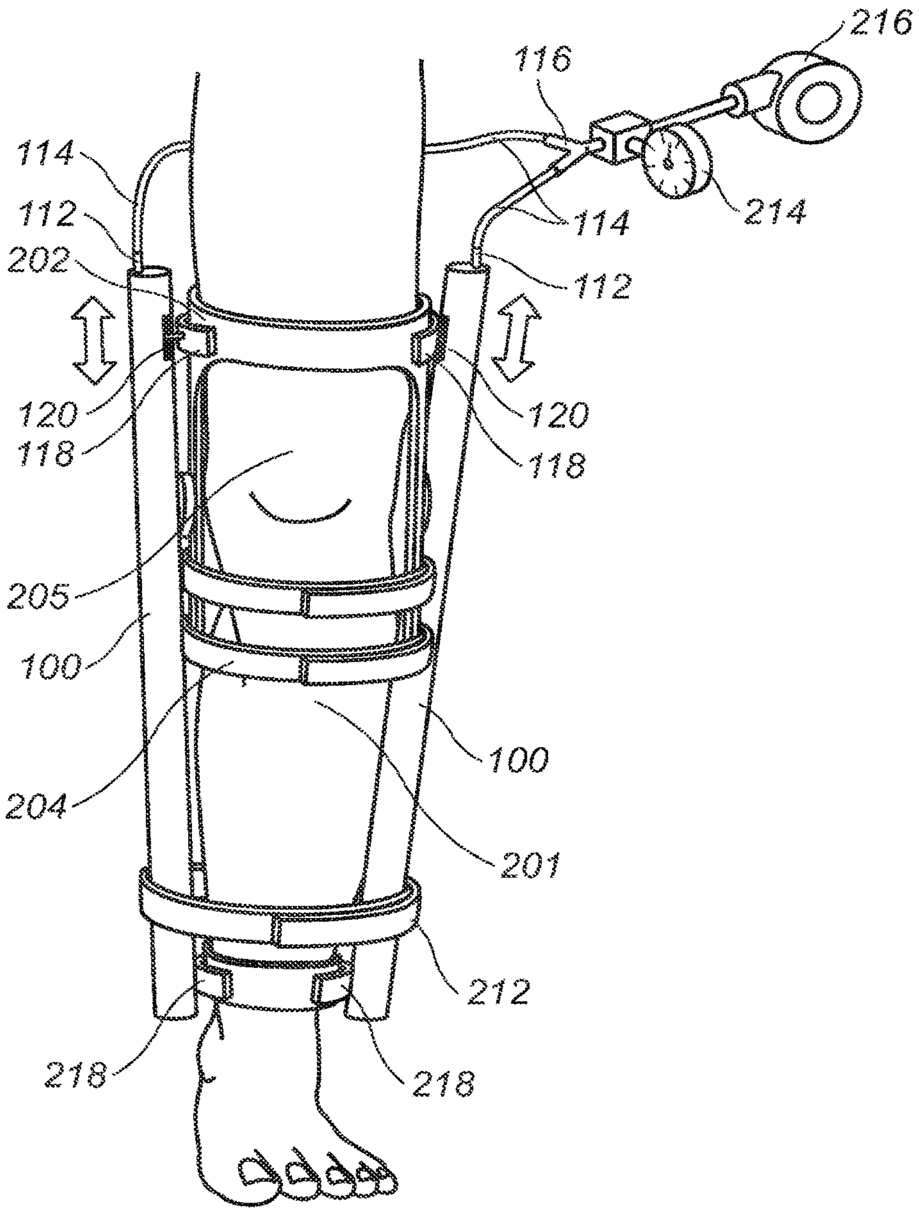
FIG. 1A is a front drawing of an embodiment of the invention showing the knee distractor in position on a leg.

Referring to the drawings, FIG. 1A illustrates a leg 201 with a knee 205 and upper knee brace 202 and lower knee brace 204. Knee stretch cylinders 100 are attached on each side of a leg where connectors 118 are fitted with side straps on the braces 202/204. In use, the lower section of the brace 204 is loosened to allow some small movement upward, and the upper section is secured. The lower section of the tube is removably attached to an ankle brace 212 by a suitable connector, 218, (much like connector 118) and does not move during use.

Figure 1B:
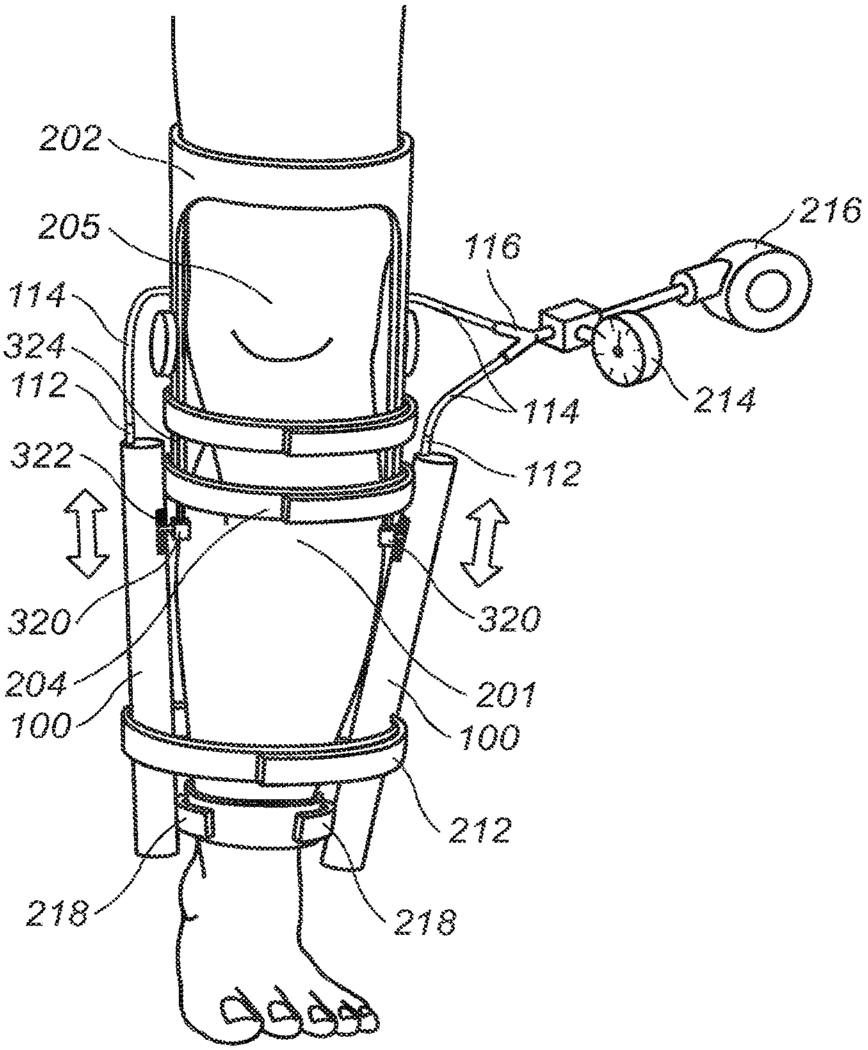
FIG. 1B is a front drawing of another embodiment of the invention showing the knee distractor in position on a leg.
Figure 1C:
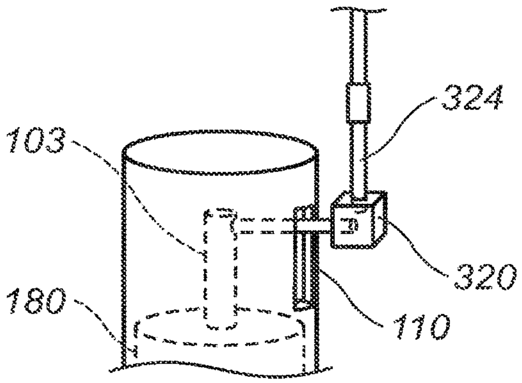
FIG. 1C is a front drawing of another embodiment of the invention showing details of the connection between the knee and cylinder tube.

FIGS. 1B and 1C illustrate another embodiment of the system. In this embodiment, the piston extension 110 connects to a connection member 320 and 322 that has a slot (or other connection means) to receive a side brace of a flexion controller (means to set knee bend positions). It is not required that the connection 320 be able to permanently attach to brace side member 324 through 322 since the action is always upward. Rather, it is only necessary that the connection allow 110 to push brace member 324 upward in cylinder 180.

This embodiment allows the brace to be set for limited movement of the knee (as often required to keep the knee joint from fully straightening) and be pushed upward with the knee in the limited (as for example, slightly bent) position to, for example, separate the joint members without completely straightening the knee joint.

Patents describing a mechanical flexion set means include U.S. Pat. Nos. 5,672,152, 5,827,208, and 7,235,059, the relevant disclosures of which are incorporated herein by reference. Pressure sensors or gauges fluidly connected to the pistons will allow an optional processor 221 operably coupled to the pump 216 to control extension by providing the processor needed feedback as to pressure, higher pressure extending the pistons further.

Conduits (such as tubing) 114 extend from the knee stretch cylinder 100 (also shown as 101) (see FIG. 2) to a Y connector 116 that is connected to the cylinder at 106 and to air pressure pump 216.

Member 214 is a pressure gauge, preferably a digital gauge. If the air pressure is processor controlled, the gauge will need to communicate with the processor 221, typically by wires or wirelessly (not shown). The gauge allows for consistent, staged, and repeated use of the device. In use in a therapy protocol, the gauge will allow return to (or alteration) of a previous treatment stretch range.

Figure 2:
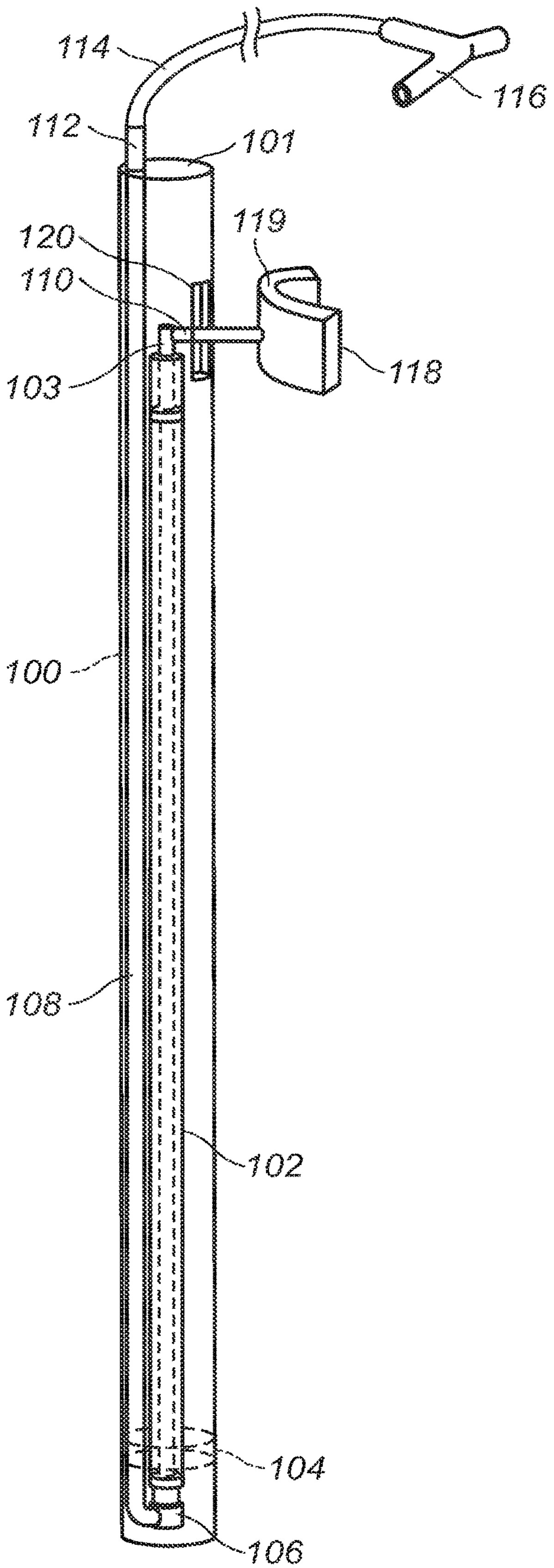
FIG. 2 is a front drawing of an embodiment of the invention showing the knee distractor components in position.

FIG. 2 shows details of the knee stretch cylinder 100, which functions as a housing for the interior cylinder 102 and piston 103 and preferably houses fluid lines 108 as well and any needed electrical or sensor wires. The housing cylinder 100 comprises a straight, unitary, unhinged, hollow tube (such as a carbon or metal tube) in which is disposed a straight unhinged unitary mechanical pneumatic cylinder 102 with an air connector 112 at the bottom and air hose 114 extending from the air hose connector 112 up through the open top of the tube.

It is important the hollow tube and cylinder be configured so as not to bend in use so that the extension of the leg will be properly accomplished. The pneumatic cylinder 102 is attached to housing cylinder 100 at the lower section of the tube at point 104. It is preferred that the pneumatic cylinder piston 103 be spring-loaded so that when no air pressure is applied, it will return to its starting position, returning the joint to a bent position.

The pneumatic (or hydraulic) cylinder 102 has a piston 103 and a horizontally (at right angles to the length of the cylinder) arranged rod 110 that extends through a slot 120 in the tube 108. The rod is connected to a brace connector 118, a semicircular member that has a slot 119 into which fits a side arm of a knee brace.

When the pneumatic cylinder is activated, the piston moves upward causing the rod and therefore the connector 118 to move upward putting tension between the upper brace and ankle brace, thus stretching the knee joint. In general, the slot 120 and therefore the travel of the rod upward will be about 1 to 4 inches, with 1 to-2 inches preferred. Of course, this will vary with the joint being treated.

The air hoses 114 that feed the pneumatic cylinder are connected to flexible conduits 114 that are connected by a Y connector 116 to air pump 216, which may be controlled by optional processor 221. Not detailed is a user interface which would allow the user to set desired tension, speed, cycle time and the like.

The upper knee brace is secure so that when the piston is extended, the space between the ankle brace 212 and the upper knee brace 202 is likewise extended, putting tension on the knee joint and thereby stretching it. This accomplishes the desirable uncoupling or straightening of the joint. Thus, if the knee is bent, adding pressure will extend the pistons, and thereby straighten the leg. Removing pressure will allow the pistons to return to a compressed condition, and that action will allow the joint to return to its bent position.

Figure 4:
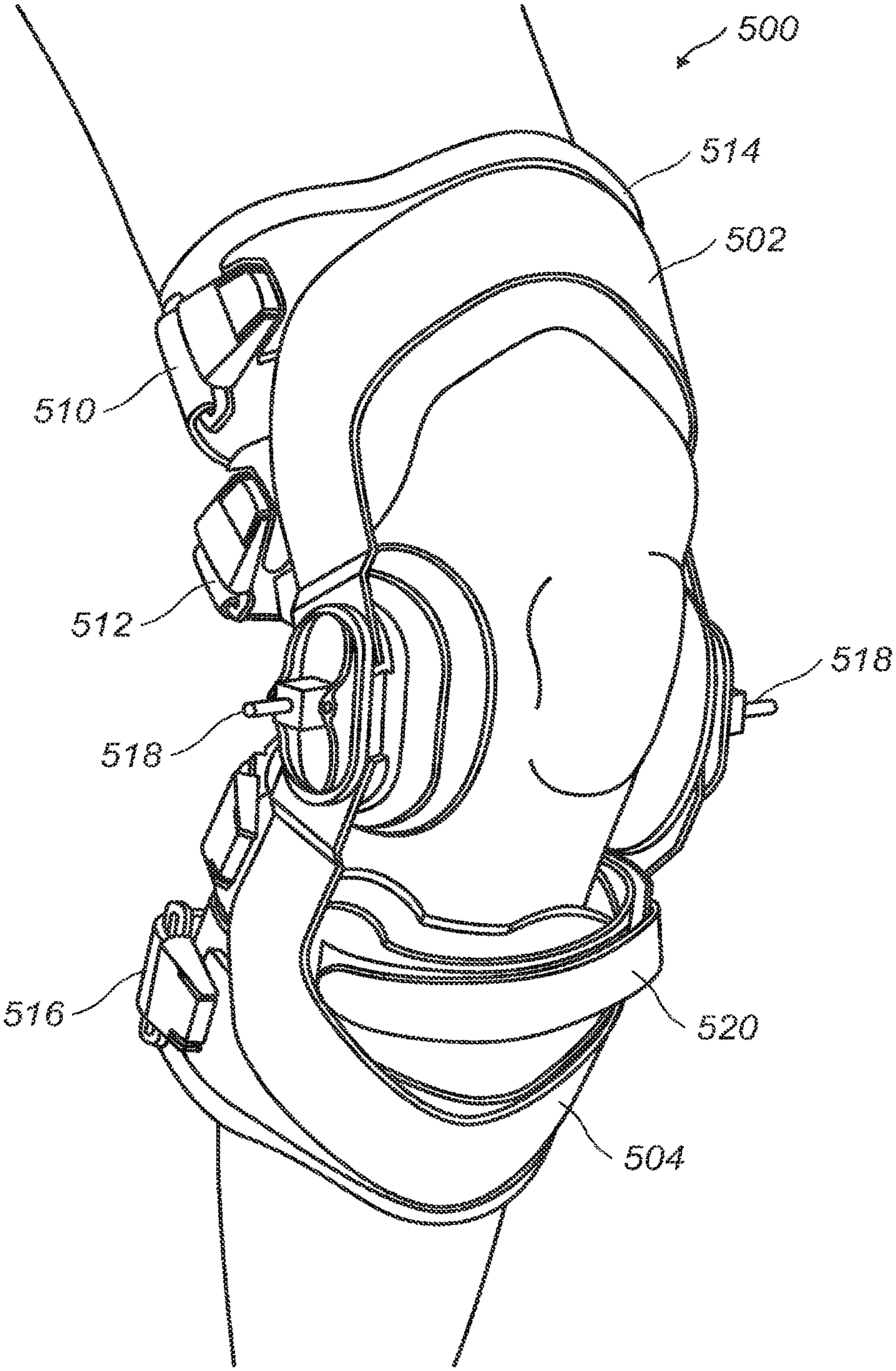
FIG. 4 is a perspective view of a knee brace suitable for of an embodiment of the invention.

FIG. 4 is an illustration of a suitable knee brace. There is a connection (118 to 518 on each side of the brace) attaching the cylinder tube (as 100 in FIG. 1) to the vertical side traps, 502, of the brace, which generally are only required to hold the strap in upward movement. Additionally, there are leg wrap bands 514 that can be latched via 510, 512 and 516 to tighten the brace 500 around the leg above and below the knee 205. Hook and loop straps 520 and 504 are also used to secure the brace to the leg.

Reaction braces from DonJoy™ can be adapted to be very suitable for use herein. In use, the knee brace will be loosened below the knee 205 to allow the more secure top section above the knee to be pushed upward by the cylinder action, thus extending the distance between the knee and ankle and ultimately distracting the knee joint.

Figure 3A:
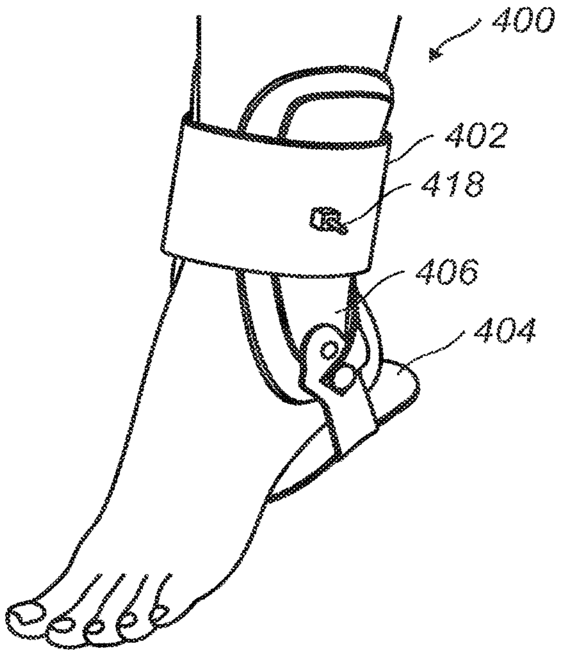
FIG. 3A is a perspective view of an ankle brace suitable for an embodiment of the invention.
Figure 3B:
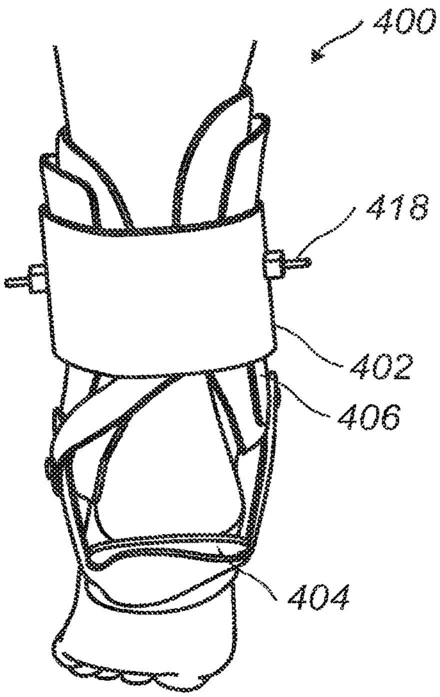
FIG. 3B is another perspective view of an ankle brace suitable for an embodiment of the invention.

FIGS. 3A and 3B illustrate a suitable ankle brace 400. As with the knee braces, there will be a connection (218 to 418 on each side of the brace) attaching the housing cylinder tube (as 100 in FIG. 1) to the sides of the brace. This ankle brace has a band 402 and side pads 406 and an underfoot pad 404. Generally, it is only required to hold the brace in position to allow the ankle to be forced downward when the cylinder 100 is extended. In most ankle braces, it is preferred that the foot be placed in a shoe with the brace disposed inside the shoe, in order to ensure the connection to the ankle is secure. An ankle cuff can also be used in the same way as an ankle brace. Suitable ankle braces include T2 Multi-Sport Ankle Brace from Active Ankle™.

Suitable cylinders include those available from Automation Direct (cylinders a07020sp—9/16 bore or a07020sp—7/16 bore), preferably those with a spring return.

Suitable hand air pumps include Silverline elite hand pump model 3mitmv8510 available from ToolTopia.

Suitable electric pumps include any of the cyclical pumps already in use in the medical arts, such as the pumps used with the VOCIC™ alternating air pressure mattress, the Micro DC™ air compressor pump in the Air Wave Pressure Therapy Device by BODENFLOW™, and the like. A peristaltic pump may also be suitable if the pressures are calibrated correctly for the cylinders in use, and the inter-bolus pressure is low enough to allow the pistons to retract.

Although only ankle and knee distraction braces are detailed herein, the principles are easily applied to any joint large enough to brace a pair of pistons in position so as to provide distraction (e.g., elbows) and if sufficiently miniaturized, the device may be applied to fingers and the like.

Method of Use

Generally, the apparatus will be fitted by an orthotic surgeon, physical therapist, or athletic/fitness trainer. The apparatus assembly will be fitted and attached to relevant joint, herein the knee and ankle braces. When properly adjusted, the assembly is tested and characteristics plotted by measuring the extension for a given pressure applied. The air pump (or hydraulic, if used) will be applied at various pressures—e.g. 2, 5, 8, 10 psi, and the displacement (and stretch) of the piston travel (distance from knee brace attachment to ankle brace attachment) measured.

Characteristic Chart
(Illustrative)

| Pressure | psi Displacement, cm |
|---|---|
| 2 | 0.5 |
| 4 | 1.1 |
| 6 | 1.8 |
| 8 | 2.4 |
| 10 | 2.8 |
| 12 | 3.0 |
| 14 | 3.1 |

Figure 5:
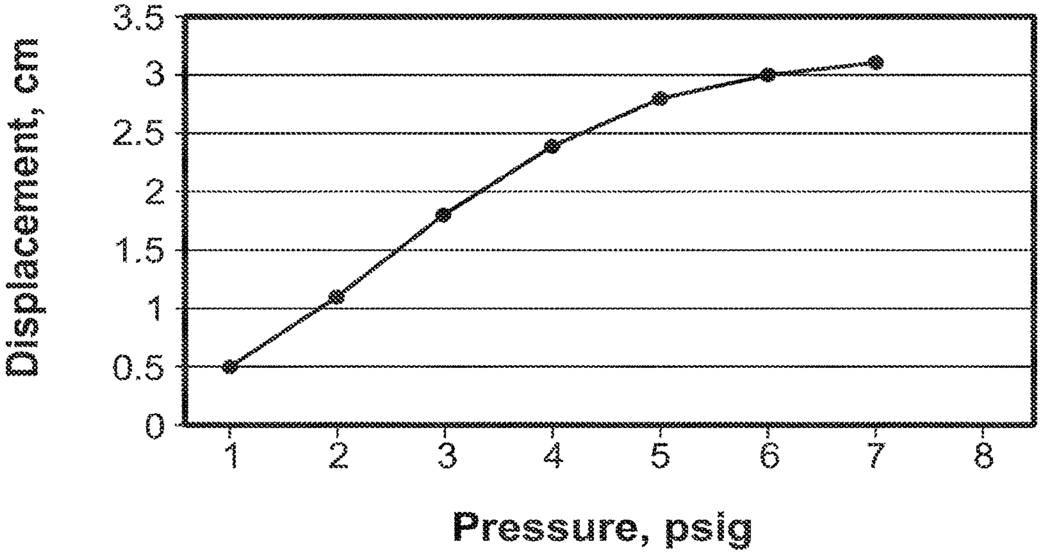
FIG. 5 is graphical plot showing relationship between displacement and applied pressure of a cylinder of an embodiment of the invention.

A characteristic curve such as illustrated in FIG. 5 can be generated for each apparatus/use combination. Using the characteristic curve, a set of user protocols can be prescribed. The user can then use the assembly at any convenient place and time without needing to visit a therapy facility.

If a knee-lock brace is used (one that locks into a predetermined position), the practitioner, physical therapist, or athletic/fitness trainer will specify (and/or set) the brace knee position lock means in the desired treatment position of the knee joint.

In the foregoing specification, the invention has been described with reference to specific embodiments thereof. It will, however, be evident that various modifications and changes can be made thereto without departing from the broader spirit and scope of the invention as set forth in the appended claims. In particular, although we have focused on knee and ankle distractors herein, the same principles can be easily applied to any joint, such as elbow, shoulder, leg, fingers, etc. All that is needed is that the device is resized accordingly to the joint to be treated and the appropriate attachment braces provided. The specification and drawings are, accordingly, to be regarded in an illustrative rather than a restrictive sense. Therefore, the scope of the invention should be limited only by the appended claims.

The invention claimed is:

1. A system for the distraction of a joint, said system comprising:

a) an upper brace configured to attach above a joint on a patient with an injury to said joint;

b) a lower brace configured to attach below said joint;

c) a first cylinder having a first extendable piston therein, said first cylinder attached at a top end to a left side of said upper brace and attached at a bottom end to a left side of said lower brace;

d) a second cylinder having a second extendable piston therein, said second cylinder attached at a top end to a right side of said upper brace and attached at a bottom end to a right side of said lower brace;

e) said upper brace not connected to said lower brace except via said first and second cylinders;

f) a pump for applying pressure to activate said first and second cylinders to extend said first and second pistons, thereby distracting said joint when said pressure is applied.

2. The system of claim 1, wherein said first and second cylinders are each pneumatic cylinders and said pump is an air pump fluidly coupled to said first and second cylinders.

3. The system of claim 1, wherein said first and second pistons are spring loaded so as to return to an unextended position when not activated.

4. The system of claim 1, further comprising first and second flexion set devices operably coupled to said first and second pistons for setting a desired length of piston extension.

5. A method of distraction of a joint, said method comprising:

a) placing the system of claim 4 over an injured joint such that said upper brace is affixed above said joint, and said lower brace is affixed below said joint and said first and second cylinders are disposed on a right and left side of said joint, respectively;

b) setting said first and second flexion set devices to a desired length of piston extension;

c) activating said pump to apply pressure to said first and second cylinders, thereby extending said first and second pistons and said joint; and d) deactivating said pump to reduce said pressure, thereby retracting said first and second pistons and said joint;

e) optionally repeating steps b and c for a period of time; and f) thereafter removing said system from said joint.

6. The system of claim 1, wherein a degree of piston extension is controlled by an amount of pressure applied by said pump.

7. The system of claim 6, wherein said amount of pressure is controlled by a processor operably coupled to said pump and to a pressure gauge configured to measure said amount of pressure.

8. The system of claim 1, wherein said first and second cylinders further comprise first and second housings containing said first and second cylinders, respectively.

9. The system of claim 8, wherein said first and second housings further contain fluid conduits connecting said pump to said first and second cylinders, respectively.

10. A method of distraction of a joint, said method comprising:

a) placing the system of claim 1 over an injured joint such that said upper brace is affixed above said joint, and said lower brace is affixed below said joint and said first and second cylinders are disposed on a right and left side of said joint, respectively;

b) activating said pump to apply pressure to said first and second cylinders, thereby extending said first and second pistons and said joint; and c) deactivating said pump to reduce said pressure, thereby retracting said first and second pistons and said joint;

d) optionally repeating steps b and c for a period of time; and e) thereafter removing said system from said joint.

11. A system for distraction of a joint, said system comprising:

a) an upper brace configured to attach above a joint on a patient with an injury in said joint;

b) a lower brace configured to attach below said joint;

c) a first cylinder having a first extendable piston therein, said first cylinder attached at a top end to a left side of said upper brace and attached at a bottom end to a left side of said lower brace;

d) a second cylinder having a second extendable piston therein, said second cylinder attached at a top end to a right side of said upper brace and attached at a bottom end to a right side of said lower brace;

e) said upper brace not connected to said lower brace except via said first and second cylinders; and f) a pump for applying pressure to activate said first and second cylinders to extend said first and second pistons, thereby distracting said joint when said pressure is applied;

g) said first and second pistons being spring loaded so as to return to an unextended position when not activated.

12. The system of claim 11, wherein said first and second cylinders are each pneumatic and said pump is an air pump fluidly coupled to said first and second cylinders.

13. The system of claim 11, further comprising first and second flexion set devices operably coupled to said first and second pistons, respectively, said first and second flexion set devices for setting a desired length of piston extension.

14. A method of distraction of a joint, said method comprising:

a) placing the system of claim 13 over an injured joint such that said upper brace is affixed above said joint, and said lower brace is affixed below said joint and said first and second cylinders are disposed on a right and left side of said joint, respectively;

b) setting said first and second flexion set devices to a desired length of piston extension;

c) activating said pump to apply pressure, thereby extending said first and second pistons and said joint; and d) deactivating said pump to reduce said pressure, thereby retracting said first and second pistons and said joint;

e) optionally repeating steps b and c for a period of time; and f) thereafter removing said system from said joint.

15. The system of claim 11, wherein a degree of piston extension is controlled by an amount of pressure applied by said pump.

16. The system of claim 15, wherein said amount of pressure is controlled by a processor operably coupled to said pump and a pressure gauge configured to measure said amount of pressure.

17. The system of claim 11, wherein said first and second cylinders further comprise first and second housings containing said first and second cylinders, respectively.

18. The system of claim 17, wherein said first and second housings further contain fluid conduits connecting said pump to said first and second cylinders, respectively.

19. A method of distraction of a joint, said method comprising:

a) placing the system of claim 11 over an injured joint such that said upper brace is affixed above said joint, and said lower brace is affixed below said joint and said first and second cylinders are disposed on a right and left side of said joint, respectively;

b) activating said pump to apply pressure, thereby extending said first and second pistons and said joint; and c) deactivating said pump to reduce said pressure, thereby retracting said first and second pistons and said joint;

d) optionally repeating steps b and c for a period of time; and e) thereafter removing said system from said joint.

* * * * *